United States Patent
Georgiou et al.

(10) Patent No.: US 12,102,303 B2
(45) Date of Patent: Oct. 1, 2024

(54) METHOD AND APPARATUS FOR DIRECT IN-VIVO, ELECTRICAL AND CHEMICAL MONITORING AND STIMULATION OF THE ENDOMETRIAL CAVITY

(71) Applicant: Gynetronics Ltd., Nicosia (CY)

(72) Inventors: Julius Georgiou, Nicosia (CY); Vasilios Tanos, Nicosia (CY)

(73) Assignee: Gynetronics Ltd., Nicosia (CY)

( * ) Notice: Subject to any disclaimer, the term of this patent is extended or adjusted under 35 U.S.C. 154(b) by 508 days.

(21) Appl. No.: 16/839,958

(22) Filed: Apr. 3, 2020

(65) Prior Publication Data
US 2020/0315593 A1 Oct. 8, 2020

Related U.S. Application Data

(60) Provisional application No. 62/829,786, filed on Apr. 5, 2019.

(51) Int. Cl.
*A61B 5/00* (2006.01)
*A61B 5/01* (2006.01)
(Continued)

(52) U.S. Cl.
CPC ............ *A61B 10/0012* (2013.01); *A61B 5/01* (2013.01); *A61B 5/0537* (2013.01); *A61B 5/273* (2021.01);
(Continued)

(58) Field of Classification Search
CPC ........... A61B 5/033; A61B 5/035; A61B 5/43; A61B 5/4306; A61B 5/4318;
(Continued)

(56) References Cited

U.S. PATENT DOCUMENTS 4,557,460 A 12/1985 Nakase
5,496,360 A 3/1996 Hoffmann et al.
(Continued)

FOREIGN PATENT DOCUMENTS

DE 102011051091 12/2012
DE 102011051112 12/2012
(Continued)

OTHER PUBLICATIONS

International Search Report and Written Opinion for related International Application No. PCT/IB2020/053225; action dated Jul. 6, 2020; (17 pages).
(Continued)

*Primary Examiner* — Joseph A Stoklosa
*Assistant Examiner* — Brian M Antiskay
(74) *Attorney, Agent, or Firm* — The Roy Gross Law Firm, LLC; Roy Gross

(57) ABSTRACT

Devices, systems and related methods for direct and in-vivo monitoring and stimulation of the endometrial cavity include a plurality of sensing modalities incorporated on a set of flexible conductive filaments that allows its insertion in an endometrial cavity through the vagina. The flexible set of conductive filaments is in direct contact with the endometrium to maximize recording sensitivity and acquire direct readings, which correspond to the functionality of the endometrium and/or electrically stimulate endometrial peristalsis in a controlled manner. The same electrodes can be used for a controlled stimulation to strengthen weakened muscle tissue before and after medical and surgical interventions on the uterus, to reset to normal contractility. The methods and systems disclosed herein can be used to improve the chances of success for artificial insemination, including in-vitro fertilization, embryo transfer, and intrauterine insemination,
(Continued)

diagnostic tests, and may further improve the overall understanding of endometrial functionality.

19 Claims, 7 Drawing Sheets

(51) Int. Cl.
    *A61B 5/0537*     (2021.01)
    *A61B 5/273*     (2021.01)
    *A61B 5/296*     (2021.01)
    *A61B 10/00*     (2006.01)
    *A61N 1/05*     (2006.01)

(52) U.S. Cl.
    CPC ............ *A61B 5/296* (2021.01); *A61B 5/4325* (2013.01); *A61B 5/6875* (2013.01); *A61N 1/0521* (2013.01); *A61B 2010/0016* (2013.01)

(58) Field of Classification Search
    CPC ... A61B 5/4325; A61B 5/4437; A61B 5/4356; A61B 5/01; A61B 5/068; A61B 5/0878; A61B 5/14503
    USPC ................. 600/372–373, 377, 376, 393, 435
    See application file for complete search history.

(56) References Cited

U.S. PATENT DOCUMENTS

| | | | | |
|---|---|---|---|---|
| 5,566,680 | A * | 10/1996 | Urion | A61B 5/035 600/561 |
| 7,844,345 | B2 * | 11/2010 | Boling | B22F 3/10 607/116 |
| 8,060,195 | B2 * | 11/2011 | Gurewitsch | A61B 5/0538 600/304 |
| 2003/0088204 | A1 | 5/2003 | Joshi | |
| 2004/0193028 | A1 * | 9/2004 | Jones | A61B 5/14542 600/361 |
| 2007/0138027 | A1 * | 6/2007 | Dinsmoor | G01N 27/4035 205/787.5 |
| 2007/0215163 | A1 * | 9/2007 | Harrington | A61B 17/12109 128/831 |
| 2014/0132302 | A1 | 5/2014 | Nagel | |
| 2014/0180169 | A1 | 6/2014 | Peters et al. | |
| 2015/0216472 | A1 * | 8/2015 | Aina-Mumuney | A61B 5/435 600/476 |
| 2017/0128053 | A1 | 5/2017 | Nakamura et al. | |
| 2017/0164867 | A1 * | 6/2017 | Kassab | A61B 5/6851 |
| 2018/0036072 | A1 * | 2/2018 | Mathur | A61B 18/18 |
| 2018/0339320 | A1 * | 11/2018 | Holmes | A61B 5/4839 |

FOREIGN PATENT DOCUMENTS

| | | | |
|---|---|---|---|
| EP | 2632328 | A | 5/2012 |
| EP | 2861145 | B1 | 7/2019 |
| GB | 2143332 | A | 2/1985 |
| WO | 2007092860 | A2 | 8/2007 |
| WO | 2007092860 | A3 | 8/2007 |
| WO | 2012058289 | A2 | 5/2012 |
| WO | 2012058289 | A3 | 5/2012 |
| WO | 2012070569 | A1 | 5/2012 |
| WO | 2012168250 | | 12/2012 |
| WO | WO-2020202108 | A1 | 10/2020 |

OTHER PUBLICATIONS

Ahmed Shafik; "Electrohysterogram: Study of the electromechanical activity of the uterus in humans"; Eur. J. Obstet. Gynecol. Reprod. Biol. 73, 85-89 (1997); https://www.ejog.org/article/S0301-2115(97)02727-9/pdf; (9 pages).

European Search Report—Appln. No. 20189700.6-1211 dated Jan. 26, 2021—6 pages.

IEC Technical Specification Photovoltaic (PV) modules—Test methods for the detection of potential-induced degradation—Part 1-1: Crystalline silicon—Delamination; Edition 1.0 2020-01 ISBN 978-2-8322-7693-8—XP82020115A-1—20 pages.

European Office Action issued in European Application No. 20718824.4 mailed Jul. 17, 2023, 6 pages.

* cited by examiner

METHOD AND APPARATUS FOR DIRECT IN-VIVO, ELECTRICAL AND CHEMICAL MONITORING AND STIMULATION OF THE ENDOMETRIAL CAVITY

PRIORITY CLAIM

This application claims priority to U.S. Provisional Application No. 62/829,786, entitled "Method and apparatus for direct in-vivo, electrical and chemical monitoring and stimulation of the endometrial cavity", filed Apr. 5, 2019, then entire contents of which are incorporated herein by reference and relied upon.

BACKGROUND

The general activity of the uterus, including various physiological phenomena associated with the uterus, has been under investigation for more than 150 years. Most attempts to monitor uterine activity involve placing a transducer on a woman's abdomen and sensing the changes in pressure and/or electrical activity through the skin. This is typically applicable for pregnant women where the intensity of the uterine activity is large enough to be detected externally; furthermore, the skin with pregnant women is stretched such that the thickness of the skin is decreased to a minimum. Several correlations for preterm labor and pregnancy complications have been established through the vast number of studies of the mechanical and electrical activity of the uterus.

The main technique used today to predict preterm labor is called tocodynamometry (TOCO), which involves a force measuring device. Unfortunately, most clinicians restrict its use to the time period before twenty six weeks' gestation. Furthermore, the exponential rise of obesity in world population has significantly reduced the ability to monitor uterus contractions using TOCO, due to the thickening of the abdominal skin.

Other techniques, such as those described in U.S. Patent Publication No. 2014/0180169A1 and U.S. Patent Publication No. 2015/0216472A1 involve the insertion of a device into the vagina, up to the point where a secure electrical connection is established with the cervix. These techniques focus on the monitoring of the electrical activity of the uterus at the cervix, which is mostly the result of the myometrium contractions commonly called electrohysterography (EHG). These techniques are, likewise, designed as a prediction method of preterm labor.

In U.S. Pat. No. 4,577,640, the same approach was adopted by placing a simple cup in the woman's vagina until it establishes a good electrical connection with the cervix. The hormone levels were continuously monitored together with the electrical activity of the uterus at the cervix. It was determined that there was a correlation between the menstrual cycle of a woman, the hormone levels including estrogen, progesterone and luteinizing hormones, and the muscular activity of the uterus. During the days of a menstrual cycle associated with ovulation, it is well known that hormone levels exhibit a spike, especially estrogen and luteinizing hormones. The same spike is identifiable by the frequency of the waves of the electrical activity monitored by the device.

U.S. Patent Publication No. 2015/0216472A1 claimed that this technique would improve the chances of success of in-vitro fertilization (IVF). Generally, the success rate of in-vitro fertilization depends highly on the condition of the endometrium and the hormone levels. This is the main reason why women are advised to take extra hormones in cases where in-vitro fertilization procedure is followed.

With this in mind, currently, there is no present methodology for taking a multichannel electrohysterograph from within the uterus, particularly for non-pregnant women, to detect the weak peristalsis signals, especially at a pre-ovulatory stage.

Specifically, a study on women with endometriosis displayed marked uterine hyperperistalsis that differs significantly from the peristalsis in unaffected women during the early, midfollicular, and midluteal phases. However, this study could not use electrical recordings to monitor the peristalsis as a suitable methodology does not exist, until now; rather, that study used vaginal sonography and MM. These techniques are disadvantageous, due to cost and related equipment required for testing. These techniques prohibit continuous, 24-hour monitoring. Furthermore it has recently been shown that uterine adenomyosis is associated with altered contractility in the myometrium.

Although the existing methods and techniques provide a glimpse into the functionality of the uterus and the connection between that functionality and several other parameters and physiological phenomena, the true conditions of the endometrial cavity have not yet been monitored directly. Thus, there still exists an unmet need for a device that can accurately measure the conditions of the endometrial cavity, whether that includes electrical activity or any other chemical or biochemical parameter, especially for long periods of continuous or nearly continuous measurement in non-clinical settings.

SUMMARY

The present invention provides a method for monitoring the endometrial electrical activity in a subject comprising: positioning a medical device within the subject, wherein at least one structural component of the device is designed to be in contact with the endometrial walls and/or endometrial cavity of the subject; receiving an electrical activity of said endometrial walls and/or cavity using at least an electrode array attached to said structural component, wherein said electrode array is in electrical contact with said endometrial walls and/or cavity, receiving an electrical activity of the endometrium and/or endometrial cavity.

In accordance with another embodiment, the present invention provides a method for monitoring the chemical content of the endometrial cavity of a subject comprising: positioning a medical device within the subject, wherein at least one structural component of the device is designed to be in contact with the endometrial walls and/or endometrial cavity of the subject; receiving an electrical signal equivalent to the sensing parameter of interest of said endometrial walls and/or cavity using at least an array of chemical and/or biochemical sensing modalities attached to said structural component, wherein said array of chemical sensing modalities are in electrical/direct contact with said endometrial walls and/or cavity, receiving an electrical signal equivalent to the sensing parameter of interest of said endometrium and/or endometrial cavity.

In accordance with an embodiment, the present invention provides a method for monitoring the environmental conditions of the endometrial cavity of a subject comprising: positioning a medical device within the subject, wherein at least one structural component of the device is designed to be in contact with the endometrial walls and/or endometrial cavity of the subject; receiving an electrical signal equivalent to the sensing parameter of interest of said endometrial walls and/or cavity using at least an array of physical sensing modalities (e.g., temperature) attached to said structural component, wherein said array of physical sensing modalities are in electrical/direct contact with said endometrial walls and/or cavity, receiving an electrical signal equivalent to the sensing parameter of interest of said endometrium and/or endometrial cavity.

In accordance with another embodiment, the present invention provides a method for identifying the time of the highest likelihood/success for embryo transfer after an in-vitro fertilization (IVF) in a subject comprising: a) positioning a flexible set of conductive filaments within the subject, wherein at least one structural component of the device is designed to be in contact with the endometrial walls and/or endometrial cavity of the subject; b) receiving an electrical signal equivalent to the sensing parameter of interest of said endometrial walls and/or cavity using at least an array of chemical and/or physical and/or biochemical sensing modalities attached to said structural component, wherein said array of chemical sensing modalities is in electrical/direct contact with said endometrial walls and/or cavity; c) receiving an electrical signal equivalent to the sensing parameter of interest of said endometrium and/or endometrial cavity; d) processing the electrical signals of said endometrium and/or endometrial cavity using signal processing techniques to translate the signal into values of the sensing parameters, e) determining the correlations of the sensed parameters of said endometrium and/or endometrial cavity, f) identifying the time during the subject's menstrual cycle with the highest likelihood of artificial reproductive technique success, when the said sensed parameters show positive correlations enabling the calculation of optimal time windows for implantation, g) transmitting an electrical stimulus to the endometrium and/or endometrial cavity for prevention and treatment of myoma (fibroids) adenomyosis and/or predict the above diseases; and h) identify high risk patients for uterine sarcoma, endometrial cancer, adenomyosis endometriosis. In this embodiment, artificial reproductive technique success can include, for example, intrauterine insemination, in-vitro fertilization, embryo transfer, and the like.

In accordance with a further embodiment, the present invention provides a method for understanding the endometrium and the endometrial cavity's functionality comprising: a) positioning a flexible set of conductive filaments within the subject, wherein at least one structural component of the device is designed to be in contact with the endometrial walls and/or endometrial cavity of the subject; b) receiving an electrical signal equivalent to the sensing parameter of interest of said endometrial walls and/or cavity using at least an array of chemical and/or physical and/or biochemical sensing modalities attached to said structural component, wherein said array of chemical sensing modalities is in electrical/direct contact with said endometrial walls and/or cavity; c) receiving an electrical signal equivalent to the sensing parameter of interest of said endometrium and/or endometrial cavity; d) processing the electrical signals of said endometrium and/or endometrial cavity using signal processing techniques to translate the signal into values of the sensing parameters, e) determining the correlations of the sensed parameters of said endometrium and/or endometrial cavity; and f) identifying the mechanisms controlling the said endometrium functionality and understand how the said functionality is related to the fertility of the subject.

In accordance with an embodiment, the present invention provides a method for stimulating tissue/receptors in the endometrial cavity of a subject comprising: positioning a medical device within the subject, wherein at least one structural component of the device is designed to be in contact with the endometrial walls and/or endometrial cavity of the subject; transmitting an electrical signal to stimulate tissue. Thus, it should be appreciated that various embodiments contemplate sensing, or stimulation, or both sensing and stimulation.

In accordance with an embodiment, the present invention provides a method for stimulating tissue/receptors in the endometrial cavity of a subject comprising: positioning a medical device within the subject, wherein at least one structural component of the device is designed to electronically release a substance such as hormone onto the endometrial walls and/or endometrial cavity through the use of electrical activation. Electrical activation of a release of a substance includes, but is not limited to, the heating of a material by electrical means.

Because of the array of electrodes/sensors, the directionality of the peristaltic activity can also be extracted from the data collected. For example, position-based measurements can be acquired with the devices and systems contemplated herein.

The proposed invention can be used in combination with other equipment, such as ultrasonic imaging equipment, in synchrony so as to improve diagnosis accuracy and treatment.

In light of the present disclosure, and without limiting the scope of the disclosure in any way, in a first aspect of the present disclosure, which may be combined with any other aspect listed herein unless specified otherwise, a system for in-vivo direct monitoring of an endometrial cavity includes a flexible set of insulated conductive filaments. A first end of the flexible set of insulated conductive filaments includes a plurality of connections. At least one of the plurality of connections is connected to an external electrical sensing/stimulation device that includes a data transmitter. A second end of the flexible set of insulated conductive filaments includes at least one sensing/stimulation module along its length. The flexible set of insulated conductive filaments has a width such that it will not cause pain to a subject. The at least one sensing/stimulation module includes a sensing array disposed along a length of the flexible set of insulated conductive filaments.

In second aspect of the present disclosure, which may be combined with any other aspect listed herein unless specified otherwise, the sensing/stimulation module is configured to monitor one of the chemical and biochemical content of the endometrial cavity.

In a third aspect of the present disclosure, which may be combined with any other aspect listed herein unless specified otherwise, the sensing/stimulation module is configured to monitor environmental conditions of the endometrial cavity.

In a fourth aspect of the present disclosure, which may be combined with any other aspect listed herein unless specified otherwise, the sensing/stimulation module is configured to monitor electrical activity of the endometrial cavity.

In a fifth aspect of the present disclosure, which may be combined with any other aspect listed herein unless specified otherwise, the sensing/stimulation module is fabricated using one of thin film and thick film fabrication techniques.

In a sixth aspect of the present disclosure, which may be combined with any other aspect listed herein unless specified otherwise, the first end the flexible set of insulated conductive filaments is fabricated using one of classical rigid or flex PCB fabrication techniques.

In a seventh aspect of the present disclosure, which may be combined with any other aspect listed herein unless specified otherwise, the flexible set of insulated conductive filaments has a width less than 5 mm.

In an eighth aspect of the present disclosure, which may be combined with any other aspect listed herein unless specified otherwise, the external electrical sensing/stimulation device transmits data via one of tethered or untethered transmission.

In a ninth aspect of the present disclosure, which may be combined with any other aspect listed herein unless specified otherwise, the sensing/stimulation module includes one of a semipermeable membrane that is specific to particular ions and a solid chemical that is gradually release with an electrical stimulus.

In a tenth aspect of the present disclosure, which may be combined with any other aspect listed herein unless specified otherwise, the sensing/stimulation module includes one of a micro thermocouple semiconductor junction and a temperature dependent voltage sensor.

In an eleventh aspect of the present disclosure, which may be combined with any other aspect listed herein unless specified otherwise, a method for in-vivo monitoring of an endometrial cavity includes positioning a flexible set of insulated conductive filaments within a subject, wherein at least a portion of the flexible set of insulated conductive filaments contacts a wall of an endometrial cavity of the subject. The method includes receiving an electrical signal equivalent to a sensing parameter with at least one sensing/stimulation module attached to the flexible set of insulated conductive filaments. The method includes processing the electrical signal to translate the electrical signal into the sensing parameter. The method further includes transmitting an electrical stimulus to the endometrial cavity. Finally, the method includes receiving a subsequent electrical signal equivalent to a subsequent sensing parameter with the sensing/stimulation module; and processing the subsequent electrical signal to translate the subsequent electrical signal into the subsequent sensing parameter.

In a twelfth aspect of the present disclosure, which may be combined with any other aspect listed herein unless specified otherwise, the sensing parameter and the subsequent sensing parameter are used for subsequent fertility analysis.

In a thirteenth aspect of the present disclosure, which may be combined with any other aspect listed herein unless specified otherwise, the sensing parameter and the subsequent sensing parameter are used to derive mechanisms that control uterus functionality.

In a fourteenth aspect of the present disclosure, which may be combined with any other aspect listed herein unless specified otherwise, uterus functionality can be used to improve fertility of the subject.

In a fifteenth aspect of the present disclosure, which may be combined with any other aspect listed herein unless specified otherwise, uterus functionality can be used to determine an appropriate treatment course for various uterine pathologies.

In a sixteenth aspect of the present disclosure, which may be combined with any other aspect listed herein unless specified otherwise, a method for identifying artificial insemination viability associated with a woman's optimal implantation window and menstrual cycle includes positioning a flexible set of conductive filaments within a subject, wherein at least a portion of the flexible set of conductive filaments contacts one of an endometrial wall and an endometrial cavity of the subject. The method includes receiving an electrical signal equivalent to a sensing parameter of interest of one of the endometrial wall and endometrial cavity using a sensing array attached to a structural component associated with the flexible set of conductive filaments. The method further includes processing the electrical signal to translate the electrical signal into the sensing parameter. Finally, the method includes identifying a time in the subject's menstrual cycle associated with the highest likelihood of artificial insemination success.

In a seventeenth aspect of the present disclosure, which may be combined with any other aspect listed herein unless specified otherwise, the sensing array monitors one of a chemical content and a biochemical content of the endometrium or endometrial cavity.

In an eighteenth aspect of the present disclosure, which may be combined with any other aspect listed herein unless specified otherwise, the sensing array monitors environmental conditions of the endometrium or endometrial cavity.

In a nineteenth aspect of the present disclosure, which may be combined with any other aspect listed herein unless specified otherwise, the sensing array monitors electrical activity of the endometrium or endometrial cavity.

In a twentieth aspect of the present disclosure, which may be combined with any other aspect listed herein unless specified otherwise, the sensing array monitors a velocity vector associated with electrical activity of the endometrium or endometrial cavity.

Additional features and advantages of the disclosed devices, systems, and methods are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein. Moreover, it should be noted that the language used in the specification has been principally selected for readability and instructional purposes, and not to limit the scope of the inventive subject matter.

BRIEF DESCRIPTION OF THE FIGURES

Understanding that the figures depict only typical embodiments and are not to be considered to be limiting the scope of the present disclosure, the present disclosure is described and explained with additional specificity and detail through the use of the accompanying figures. The figures are listed below.

DETAILED DESCRIPTION OF EXAMPLE EMBODIMENTS

Figure 6:
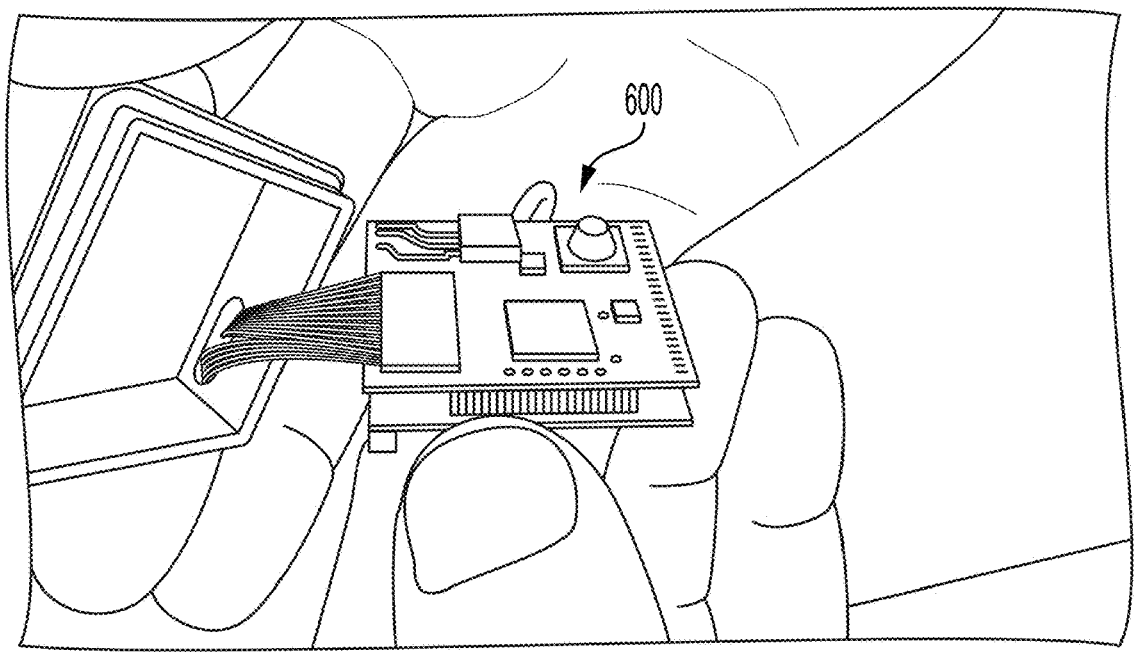
FIG. 6 illustrates a possible portable electro-utero-graph recording/stimulation device that stores the data on a micro-SD card, according to an example embodiment of the present disclosure.
Figure 7:
FIG. 7 illustrates a laptop computer displaying the signals recorded by the recording/stimulation device, according to an example embodiment of the present disclosure.

The device used along with the inventive methods herein, is described briefly as follows. FIGS. 1, 2A, 2B, 3A, 3B and 3C show the arrangement of sensing/stimulation modalities for in-vivo monitoring of the endometrial cavity. Specifically, the device 100 includes a flexible set of conductive filaments 103, encapsulated in an insulator material, having two ends. A first end includes the connection board 101 with multiple via holes 107, 108 (or a related surface mount footprint), for related coupling with an electrical connector 102 via pins 106. Connector 102 may further include single pin 105 extending from the opposite side of the connector 102, which may be configured for connection to another external electrode (or sensor) to be used as a baseline/reference for the readings or an electrical stimulation circuit. Furthermore, at least one of said via holes 107, 108 is designated for connection to at least one external sensing/stimulation device 600 (described in greater detail herein with respect to FIG. 6).

The flexible set of conductive filaments 103 includes one or more sensing/stimulation modalities 104 along its length at a second end. For example, with reference to FIG. 3C, the conductive filaments may be coated in gold or, alternatively, an other conductive material. In an embodiment, the flexible set of conductive filaments 103 and related sensing/stimulation modalities 104 have a width of less than 5 mm. By having a reduced width, such as less than 5 mm, the device 100 ensures that subsequent insertion into the endometrial cavity is safe, painless, and harmless to the patient.

In an embodiment, the sensing/stimulation modalities 104 are disposed in the form of sensing/stimulation array of conductive openings 109, 110 in an insulator along a portion of the length of the second end. In an embodiment, the conductive openings 109, 110 may be coated with a semipermeable membrane or a solid chemical that may be released gradually with the application of electric pulses.

Figure 1:
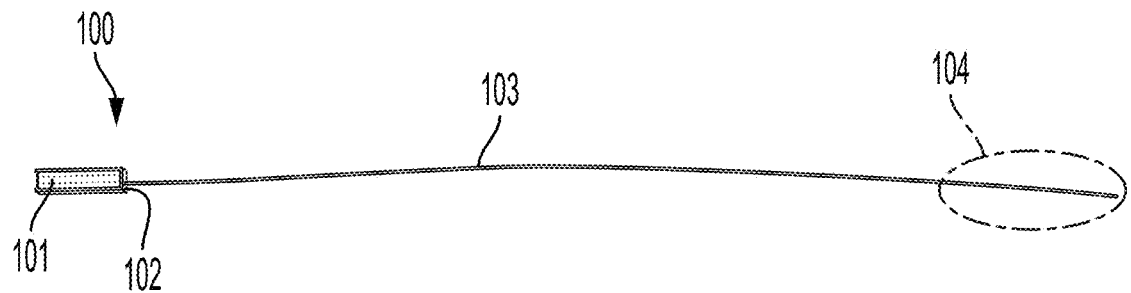
FIG. 1 illustrates the complete design of a flexible set of conductive filaments configured for insertion into a woman's endometrial cavity for monitoring and/or for stimulation, according to an example embodiment of the present disclosure.
Figure 2A:
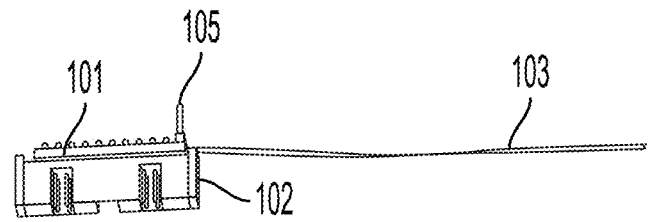
FIG. 2A and FIG. 2B illustrate a connector, including a single pin extending from the opposite side of the connector, which may be connected to another external electrode or sensor to be used as a baseline/reference for the readings or an electrical stimulation circuit, according to an example embodiment of the present disclosure.
Figure 2B:
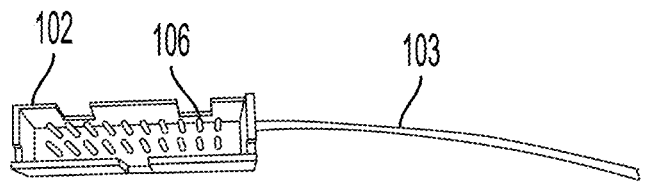
Figure 3A:
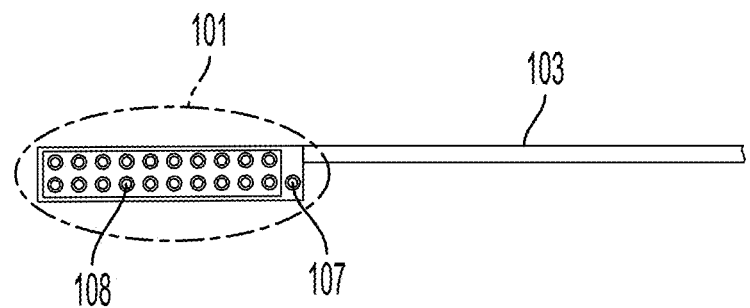
FIG. 3A and FIG. 3B illustrate a rigid section of the flexible set of conductive filaments with via holes that enable connection to the connector that will further connect to the data acquisition/stimulation system, according to an example embodiment of the present disclosure.
Figure 3B:
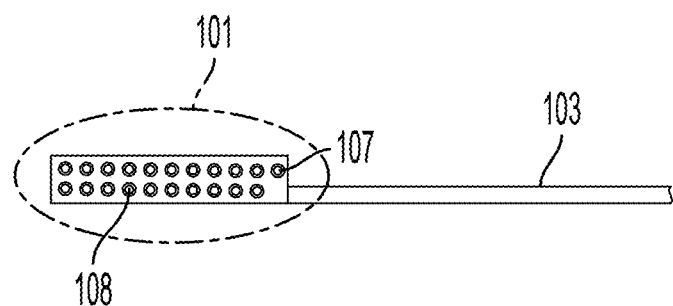
Figure 3C:
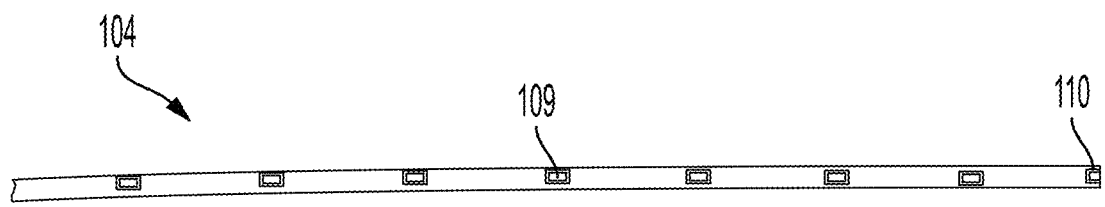
FIG. 3C illustrates one possible configuration, consisting of exposed conductive filaments coated with gold as electrodes to sense/stimulate the electrical activity in the endometrial cavity, according to an example embodiment of the present disclosure.
Figure 4:
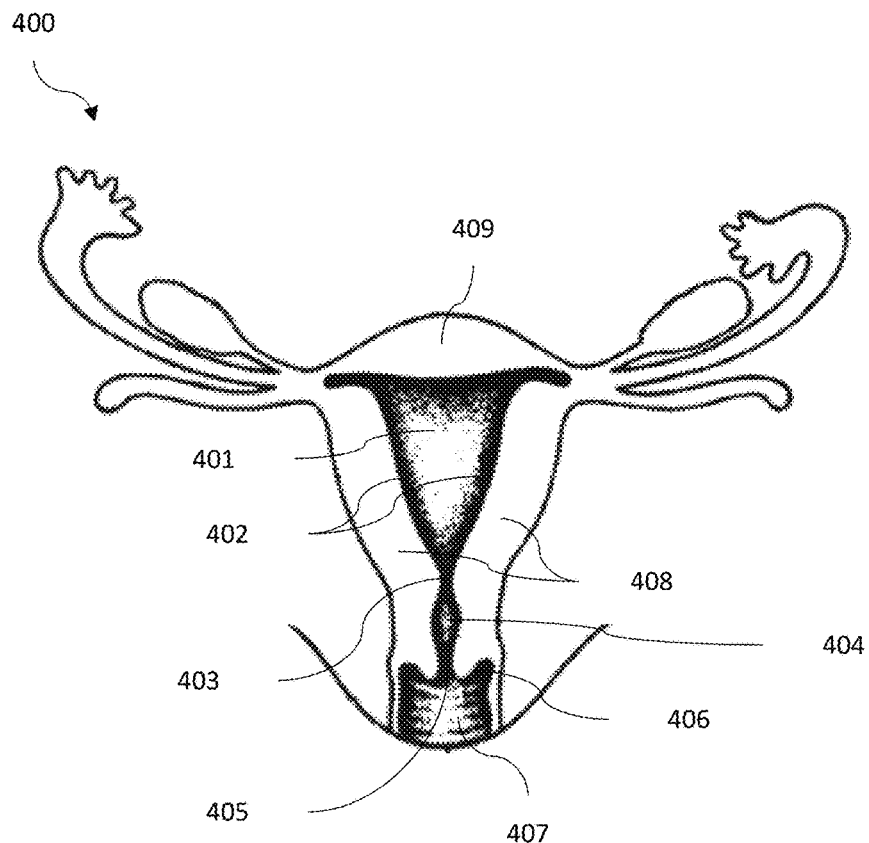
FIG. 4 illustrates the uterus and the endometrial cavity, for subsequent device insertion and sensing/stimulation, according to an example embodiment of the present disclosure.

FIG. 4 shows a schematic of a uterus 400 of a woman. The schematic shows the vagina 407, cervix 406, cervical canal 404, external orifice of the cervix 405, internal orifice of the cervix 403, myometrium 408, endometrium and endometrial walls 402, endometrial cavity 401 and the fundus 409. Once inserted (as descried in greater detail below), the flexible set of conductive filaments 103 are configured to pass electrical charge to and from the sensing/stimulation modalities 104; when inserted, the sensing/stimulation modalities 104 are configured to be disposed within a subject's endometrium 402, such that the sensing/stimulation modalities 104 are in direct and electrical contact with the endometrial walls 402 and/or endometrial cavity 401. The sensing/stimulation modalities 104 relay electrical signals to and from the connector board 101, which in turn relays information to the external sensing/stimulation device 600.

Via this system, the flexible set of insulated conductive filaments 103 are configured to record a multichannel electrical recording from within the uterus, particularly at the endometrium and/or endometrial walls 402. This multichannel electrical recording is referred to herein is an electro-utero-graph (EUG). This EUG can be used to determine uterus functionality, including an appropriate treatment course for various uterine pathologies including fibroids, adenomyosis, sub-endometrial adenomyotic cysts, and other related pathologies. The EUG can identify the magnitude of the abnormal contractility, indicating the need of myomectomy or adenomyomectomy, and related timing for said procedures.

Figure 5:
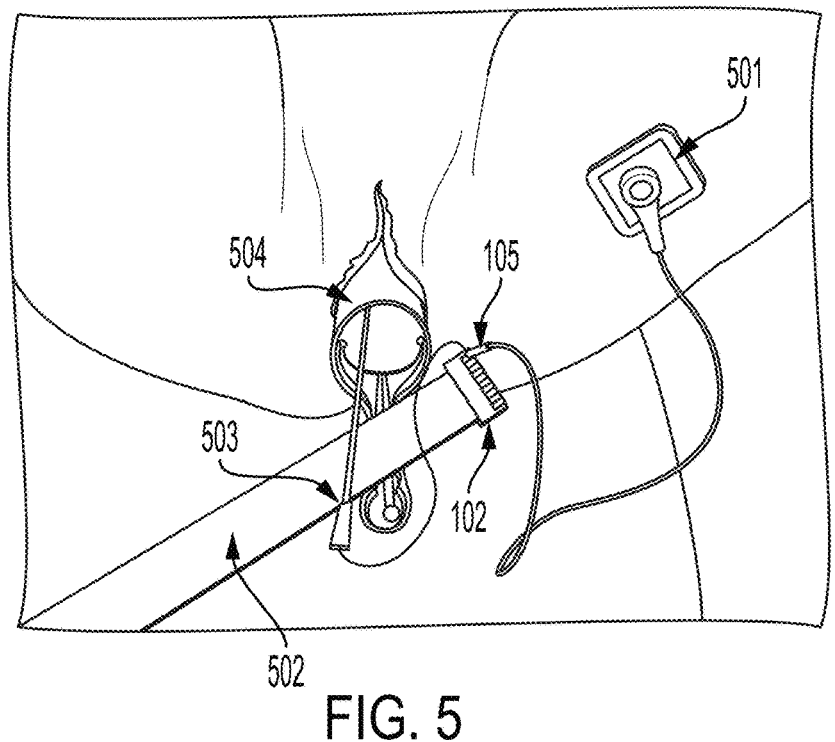
FIG. 5 illustrates an external view of the female reproductive organs with a speculum in place, the electrodes inserted into the uterus for electro-utero-graph recording and connected to a flexible ribbon cable leading to a recording device, according to an example embodiment of the present disclosure
Figure 8:
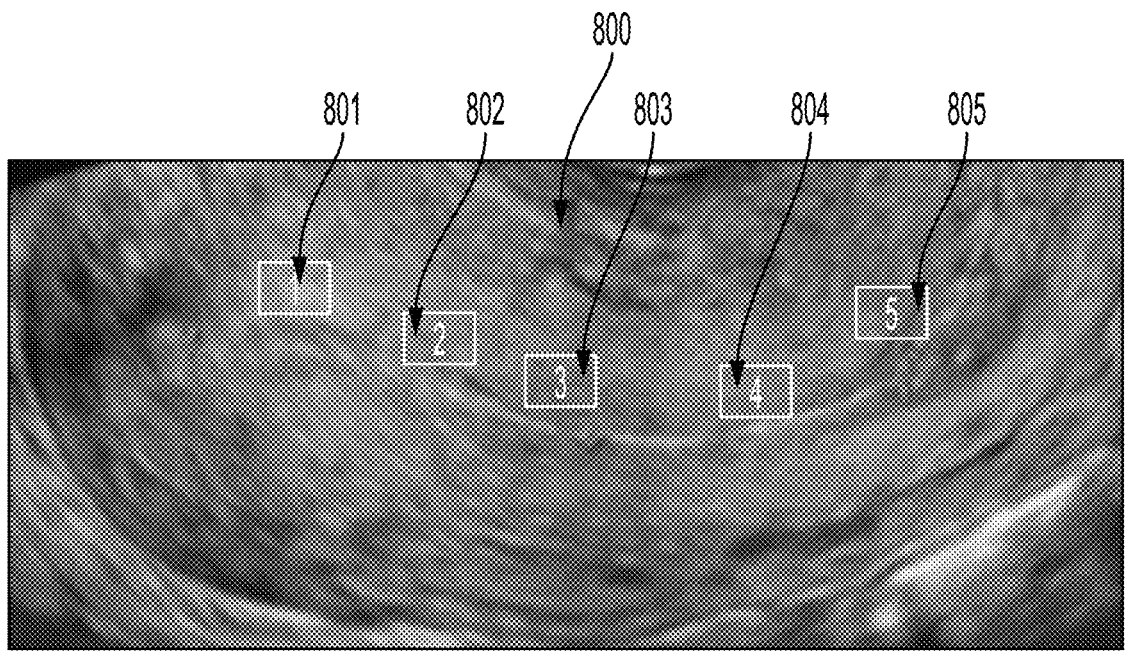
FIG. 8 illustrates an ultrasound image obtained with the flexible set of insulated conductive filaments in place, and with openings at various sites of interest, according to an example embodiment of the present disclosure.
Figure 9:
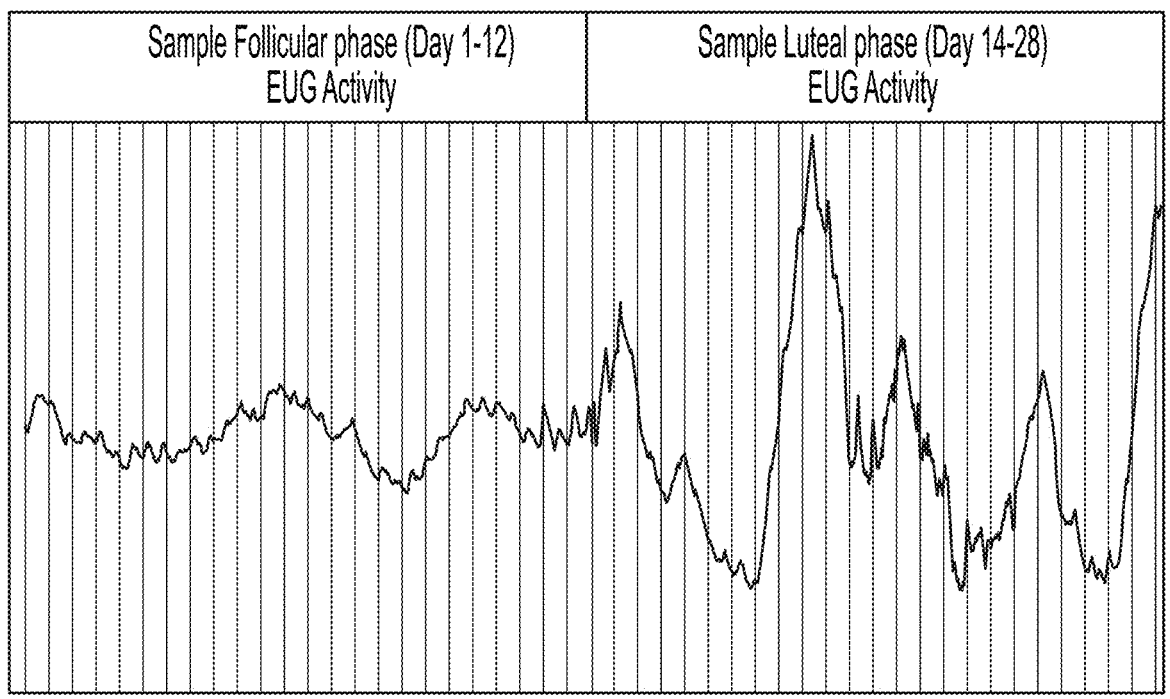
FIG. 9 illustrates some sample signals illustrating how the electro-utero-graph activity changes in the same patient, depending on the phase of the menstrual cycle, according to an example embodiment of the present disclosure.
Figure 10:
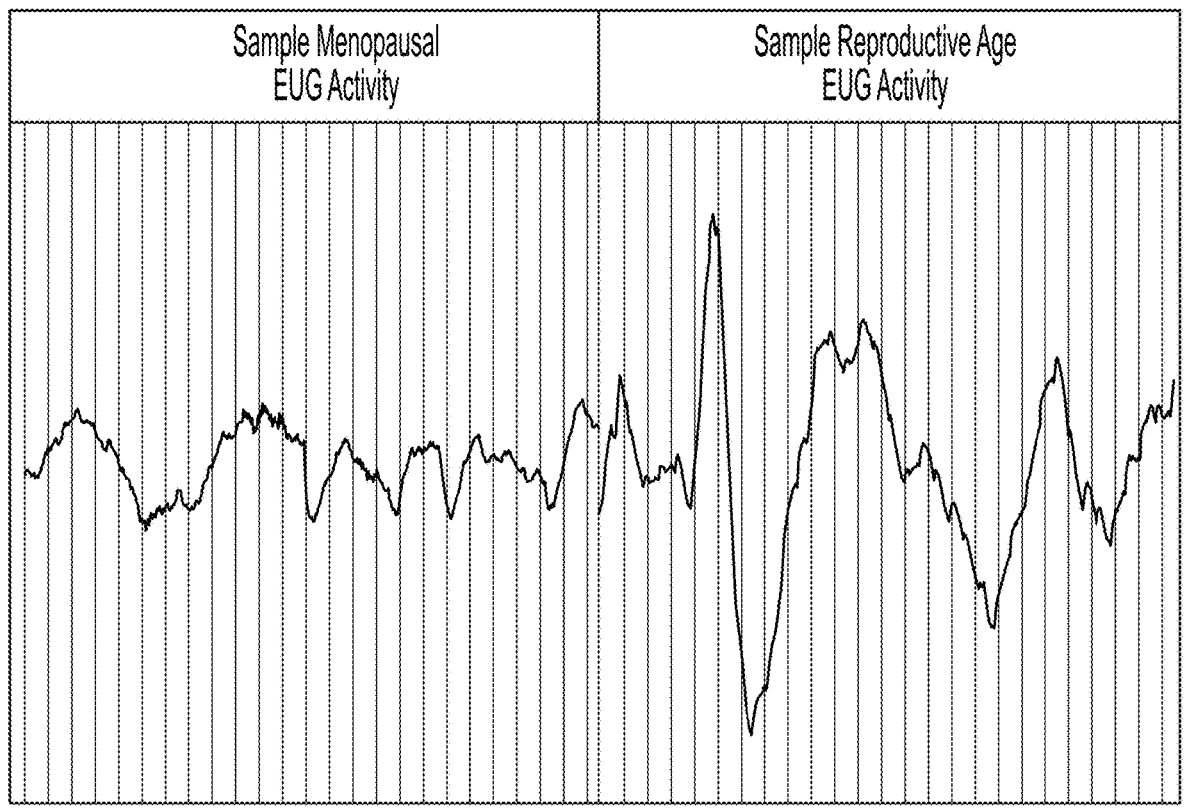
FIG. 10 illustrates some sample signals illustrating how the electro-utero-graph activity changes between different patients, depending on whether they are menopausal or of reproductive age, according to an example embodiment of the present disclosure.
Figure 11:
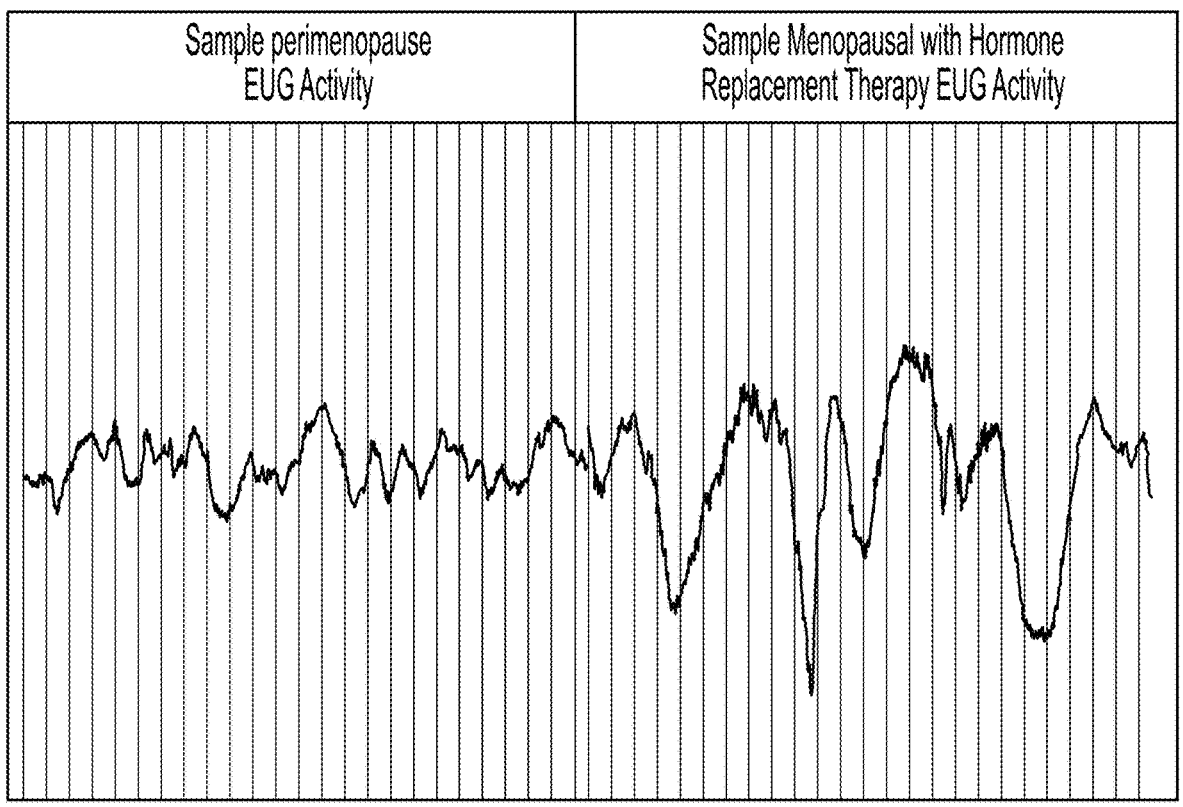
FIG. 11 illustrates some sample signals coming from a perimenopausal subject and a menopausal subject undergoing hormone replacement therapy, according to an example embodiment of the present disclosure.

An example of the procedure, with reference to FIGS. 5 and 8, to insert the sensing/stimulation modalities 104 in the endometrium 402 of the subject includes insertion of the speculum 504 and use transvaginal ultrasound to visualize 800 the vaginal walls and the external orifice of the cervix 405. The clinician will then insert an embryo transfer catheter 503, up to 3 mm from the fundus 409. Once the catheter 503 is inserted, the clinician will, insert the flexible set of insulated conductive filaments 103 including the sensing/stimulation modalities 104 and sensing/stimulation array into the embryo transfer catheter 503 until the tip of the sensing/stimulation modalities 104 reach the tip of the catheter, with a fundal sensor/stimulators being in proximity to the fundus 801, Mid Endometrial point 802, Low Endometrial point 803, cervical points 804, 805. The clinician then retracts the catheter 503 out of the endometrium 402, to expose the sensing/stimulation modalities 104 of the sensing/stimulation array to be in direct contact with the endometrial walls 402. The clinician connects electrical connector 102 to the inputs of the external sensing/stimulation device 600, via cable 502. Once the sensing/stimulation modalities 104 are exposed to the relevant anatomical features, the sensing/stimulation modalities 104 may advantageously take required readings using a data acquisition system, such as the external sensing/stimulation device 600, apply stimulation to the relevant anatomical features, or a combination of both for diagnosis, treatment, and the like. While ultrasonic guidance is described above, it should be appreciated that ultrasonic guidance is not required for the devices and methods disclosed herein.

For example, sensing/stimulation modalities 104 may measure electrical signals on or near at least one of the endometrium and endometrial walls 402; these electrical signals are provided to external sensing/stimulation device 600, for subsequent analysis and processing, to associate the electrical signals with one or more physiological parameters and/or physiological phenomena. Analysis include, for example, identification of the intensity, frequency, and direction of the various signals. Directional analysis can include, for example, whether the intensity is more directed in a cephalad direction or a caudal direction at the measurement site. Alternatively, for example, sensing/stimulation modalities 104 may apply stimulation, such as electrical stimulation, to at least one of the endometrium and the endometrial walls 402. Alternatively, for example, sensing/stimulation modalities 104 may both measure electrical signals and apply stimulation, such as measuring electrical signals on or near at least one of the endometrium and endometrial walls 402 both before and after electrical stimulation. Again, parameter detection and stimulation signal control are provided, for example, by the external sensing/stimulation device 600.

Once procedures are completed, with the use of the ultrasound for visualization, the clinician can reinsert the catheter 503 to completely cover the sensing/stimulation modalities 104, and then subsequently remove the sensing/stimulation modalities 104 out of the subject and remove the catheter 503 out of the subject.

While the embodiment above describes that the device 100 may take readings, and subsequently store these readings on the data acquisition system, such as the external sensing/stimulation device 600, it should be appreciated that additional data storage capabilities are contemplated herein. For example, the external device 600, which is a data storage device, may advantageously include a wireless transmitter, such as Bluetooth, ZigBee, Wi-Fi, or the like, for wireless transmission from external device 600 to a handheld device, such as a cell phone. Data may also be wirelessly transmitted from external device 600 to the cloud, for additional processing and/or data aggregation. Clinicians may access data on the cloud, for patient diagnosis and related data analysis; patients may access data on the cloud, for personal medical history, symptom tracking, and the like.

Advantageously, the sensing/stimulation modalities 104 are disposed along the length of the flexible set of insulated conductive filaments 103, such that the sensing/stimulation modalities 104 are configured to monitor sensing parameters with respect to a longitudinal dimension of the endometrial cavity, providing an overall high density network of sensors/stimulators and related direction-based measurement.

In the primary embodiment described above, the sensing/stimulation modalities 104 take required readings, apply stimulation to the relevant anatomical features, or a combination of both. Once readings/stimulation occur, the catheter 503 is reinserted and the entire device 100 is removed from the subject. In a different embodiment, the catheter 503 is not required to be reinserted. Rather, the device 100 remains inside the subject for 24-hour continuous monitoring. For example, after catheter 503 is initially removed, external sensing/stimulation device 600 is attachable to the first end of the flexible set of insulated conductive filaments 103 via a low or zero insertion force connector and related flexible cable. For example, a flex connector such as the SFVL Series connectors by Amphenol is used to connect device 600 to the flexible set of insulated conductive filaments 103.

Continuous data measured by the sensing/stimulation modalities 104 are stored in the external sensing/stimulation device 600. In an embodiment, device 600 is clipped onto the user's apparel, such as the user's underwear in close proximity to the insertion point, during continuous monitoring. After a particular monitoring period is completed, device 600 can wirelessly transmit data associated with the monitoring period, such as a day's worth of data, to an external device such as a cell phone. While a 24-hour monitoring period is disclosed herein, it should be appreciated that other (potentially longer) monitoring periods are contemplated. For example, device 600 could include an external power source, such as a battery, such that monitoring periods could run for indefinite lengths of time.

In a particular embodiment of the medical device 100 used with the methods of the present invention, the other side of the flexible set of conductive filaments 103 is inserted into the subject's endometrium 401 comprising: positioning a medical device within the subject, wherein the sensing/stimulation modalities 104 with the sensing array designed to be in contact with the endometrial walls 402 and/or endometrial cavity 401 of the subject; receiving an electrical activity of said endometrial walls 402 and/or cavity 401 using at least an electrode array of the said other side of the flexible set of conductive filaments 103, wherein said electrode array is in electrical contact with said endometrial walls 402 and/or cavity 401, receiving/transmitting an electrical activity, as otherwise called in the literature electrohysterography (EHG), of the endometrium 402 and/or endometrial cavity 403.

In accordance with another embodiment of the medical device used with the methods of the present invention, the flexible set of conductive filaments 103 is inserted into the subject's endometrium 401 comprising: positioning a medical device within the subject, wherein the sensing modalities 104 with the sensing array designed to be in contact with the endometrial walls 402 and/or endometrial cavity 401 of the subject; receiving an electrical signal equivalent to the sensing parameter of interest of said endometrial walls 402 (in the case of semi-permeable membrane coatings of the conductor) and/or cavity 401 using the chemical and/or biochemical sensing array of the sensing modalities 104, wherein said sensing array of chemical/biochemical sensing modalities 104 are in physical direct contact with said endometrial walls 402 and/or cavity 401, receiving an electrical signal equivalent to the sensing parameter of interest of said endometrium 402 and/or endometrial cavity 401. The levels of the sensing parameters such as pH, progesterone, luteinizing hormone, progesterone and other concentration levels of several ionic substances, together with the period in the menstrual cycle of the subject can be used to generate correlations between healthy and non-healthy subjects in terms of pathogenic diseases or even early cancer detection.

In accordance with another embodiment of the medical device used with the methods of the present invention, the other side of the flexible set of conductive filaments 103 is inserted into the subject's endometrium 401 comprising: positioning a medical device within the subject, wherein the sensing modalities 104 with the sensing array designed to be in contact with the endometrial walls 402 and/or endometrial cavity 401 of the subject; receiving an electrical signal equivalent to the sensing parameter of interest such as temperature, moisture levels, surface roughness, and the like, of said endometrial walls 402 and/or cavity 401 using the physical sensing array of the sensing modalities 104, wherein said sensing array of physical sensing modalities 104 are in electrical/direct contact with said endometrial walls 402 and/or cavity 401, receiving an electrical signal equivalent to the sensing parameter of interest of said endometrium 402 and/or endometrial cavity 401.

In accordance with a further embodiment of the medical device used with the methods of the present invention, identification of the time when the chances for embryo transfer after an in-vitro fertilization (IVF) or the timing of an intrauterine insemination are at the maximum in a subject is achieved by: a) positioning one side of a flexible set of insulated conductive filaments 103 within the subject, wherein the sensing modalities 104 with the sensing array of the device is designed to be in contact with the endometrial walls 402 and/or endometrial cavity 401 of the subject; b) receiving an electrical signal equivalent to the sensing parameter of interest of said endometrial walls 402 and/or cavity 401 using the sensing modalities 104 of chemical and/or physical and/or biochemical and/or electrical sensing array, wherein said sensing array of chemical and/or physical and/or biochemical and/or electrical sensing modalities 104 is in electrical/direct contact with said endometrial walls 402 and/or cavity 401; c) receiving an electrical signal equivalent to the sensing parameter of interest of said endometrium 402 and/or endometrial cavity 401; d) processing the electrical signals of said endometrium 402 and/or endometrial cavity 401 using signal processing techniques to translate the signal into values of the sensing parameters, e) determining the correlations of the sensed parameters of said endometrium 402 and/or endometrial cavity 401; and f) identifying the time during the subject's menstrual cycle with the highest likelihood of IVF success when the said sensed parameters show positive correlations. Other patents (US2015/0216472A1) have claimed to be able to generate correlations between the likelihood of success of IVF by monitoring only the electrical activity of the myometrium 408. This invention monitors chemical and/or physical and/or electrical parameters directly within the endometrial cavity 401 allowing for a much higher sensitivity and more reliable correlations.

In accordance with a further embodiment of the medical device used with the methods of the present invention, understanding of the functionality of the endometrium and the endometrial cavity is achieved by: a) positioning a side of a flexible set of conductive filaments 103 within the subject, wherein the sensing modalities 104 with the sensing array of the device is designed to be in contact with the endometrial walls 402 and/or endometrial cavity 401 of the subject; b) receiving an electrical signal equivalent to the sensing parameter of interest of said endometrial walls 402 and/or cavity 401 using the sensing modalities 104 of chemical and/or physical and/or biochemical and/or electrical sensing array, wherein said sensing array of chemical and/or physical and/or biochemical and/or electrical sensing modalities 104 is in electrical/direct contact with said endometrial walls 402 and/or cavity 401; c) receiving an electrical signal equivalent to the sensing parameter of interest of said endometrium 402 and/or endometrial cavity 401; d) processing the electrical signals of said endometrium 402 and/or endometrial cavity 401 using signal processing techniques to translate the signal into values of the sensing parameters, e) determining the correlations of the sensed parameters of said endometrium 402 and/or endometrial cavity 401; f) identifying the mechanisms controlling the said endometrium functionality and understand how the said functionality is related to the fertility of the subject. Although the way the endometrium 402 functions is understood by speculation and how that functionality affects the fertility of the uterus 400, there are currently no experimental, in-vivo results to prove it and moreover the mechanisms by which that functionality is controlled are yet unknown. This invention can be used to derive all the required in-vivo, experimental data to fully model and understand those mechanisms.

In accordance with a further embodiment of the medical device used with the methods of the present invention, monitoring other biological parameters of the subject is achieved by: a) positioning a side of a flexible set of conductive filaments 103 within the subject, wherein the sensing modalities 104 with the sensing array of the device is designed to be in contact with the endometrial walls 402 and/or endometrial cavity 401 of the subject; b) receiving an electrical signal equivalent to the sensing parameter of interest of said endometrial walls 402 and/or cavity 401 using the sensing modalities 104 of chemical and/or physical and/or biochemical and/or electrical sensing array, wherein said sensing array of chemical and/or physical and/or biochemical and/or electrical sensing modalities 104 is in electrical/direct contact with said endometrial walls 402 and/or cavity 401; c) receiving an electrical signal equivalent to the sensing parameter of interest of said endometrium 402 and/or endometrial cavity 401; d) processing the electrical signals of said endometrium 402 and/or endometrial cavity 401 using signal processing techniques to translate the signal into values of the sensing parameters, e) determining the correlations of the sensed parameters of said endometrium 402 and/or endometrial cavity 401 with other biological parameters of the subject; f) identifying the mechanisms associated with the correlations of the biological parameter of interest and the sensing parameter within the endometrium. Due to the fact that, the endometrium 402 and the endometrial cavity 401 have a plurality of blood vessels, several biological parameters can be monitored through the blood providing vital information on the subject's health. This information can be used to optimize the doses of Hormone Replacement Therapy (HRT) since lower doses can prevent the development of heart diseases or breast cancer.

Specifically, for example, the sensing modalities 104 disclosed herein may advantageously identify and characterize uterine peristalsis, and related physiological phenomena, including but not limited to menstrual blood clearance, endometrial rejuvenation, fertilization, implantation, early pregnancy preservation, and the like. Identification and characterization may involve both sensing of information, stimulation of pertinent anatomical features, and both sensing and stimulation; identification and characterization will typically involve additional analysis at a third party source, such as a cell phone or the cloud, once data is provided by the external device 600, for example.

Use of the verb "comprise" and its associations do not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed data acquisition and signal processing hardware as well as by means of a suitably programmed computer. Moreover, any combination of the above-described elements in all possible variation thereof is encompassed by the invention unless otherwise indicated herein or otherwise clearly contradicted by context.

As used in this specification, including the claims, the term "and/or" is a conjunction that is either inclusive or exclusive. Accordingly, the term "and/or" either signifies the presence of two or more things in a group or signifies that one selection may be made from a group of alternatives.

The many features and advantages of the present disclosure are apparent from the written description, and thus, the appended claims are intended to cover all such features and advantages of the disclosure. Further, since numerous modifications and changes will readily occur to those skilled in the art, the present disclosure is not limited to the exact construction and operation as illustrated and described. Therefore, the described embodiments should be taken as illustrative and not restrictive, and the disclosure should not be limited to the details given herein but should be defined by the following claims and their full scope of equivalents, whether foreseeable or unforeseeable now or in the future.

The invention is claimed as follows:

1. A system for in-vivo intrauterine electromyography of tissue of at least one of an endometrial cavity, an endometrial junctional zone, and an endometrium comprising:
   a flexible structure sized for insertion into said endometrial cavity, sufficiently flexible to conform to said endometrial cavity so as not to cause muscle stimulation, and having a width of less than 5 mm, including a set of insulated conductive filaments and comprising:
      a first end portion of the flexible set of insulated conductive filaments including a connector comprising a plurality of connections,
      a second end portion of the flexible set of insulated conductive filaments including an array of electrodes configured for acquiring intrauterine electromyography measurements and disposed along a length of said second end portion, wherein said electrodes are spaced apart from each other to provide a plurality passive electrical measurements, each electrode of said array providing a measurement of a different region of said tissue of said at least one of said endometrial cavity, an endometrial junctional zone, and an endometrium, which electrical measurements including measurement of electrical activity associated with uterine contractility; and
   data acquisition and signal processing hardware configured to:
      receive said plurality of electrical measurements; and
      identify and characterize non-pregnant uterine contractility using said plurality of electrical measurements.

2. The system of claim 1, wherein the second end portion includes a temperature sensor.

3. The system of claim 1, wherein, when a tip of said second end portion is positioned in proximity to a fundus of said endometrial cavity, said different regions include different regions with respect to a longitudinal dimension of said endometrial cavity.

4. They system of claim 3, wherein:
   said array of electrodes comprises a fundal electrode disposed at a tip of said flexible structure; and
   when said fundal electrode is positioned in proximity to said fundus of said endometrial cavity, said array of electrodes are spaced to provide an electrode located at a mid-endometrial region, an electrode located at a low endometrial region, and one or more electrodes located in proximity to a cervix of said endometrial cavity.

5. The system of claim 1, wherein electrodes of said array are formed by conductive filament portions revealed at openings in insulation material of said insulated conductive filaments.

6. The system of claim 5, wherein said openings comprise openings in said insulation material to different individual conductive filaments of said set of conductive filaments.

7. The system of claim 5, wherein one or more of said openings are covered with a semipermeable membrane which is specific to particular ions to be measured.

8. The system of claim 7, wherein:
   said specific ions comprise one or more of H+, Na+, K+;
   said data acquisition and signal processing hardware is configured to determine, from said plurality of electrical measurements, for one or more region as defined by position of said electrodes, one or more of:
      ion concentration of Na+;
      ion concentration of K+; and
      pH.

9. The system of claim 1, wherein said data acquisition and signal processing hardware is configured to identify one or more of intensity, frequency, and direction of measurements of said plurality of electrical measurements.

10. The system of claim 1, wherein said data acquisition and signal processing hardware is configured to determine a directionality of the uterine contractility using said plurality of electrical measurements of said different regions of said endometrial cavity and said spacing of said electrodes.

11. The system of claim 1, comprising at least one of an electrical sensing and stimulation device configured to be positioned externally to said endometrial cavity and electrically connectable to said first end portion by at least one of said plurality of connections.

12. The system of claim 11, further comprising a sensor external to at least one of said endometrium and endometrial cavity, said sensor being connected to at least one of said electrical sensing and stimulation device to provide a reference electrical measurement.

13. The system of claim 1, further comprising a power source connected to said set of conductive filaments and configured to supply electrical power to one or more electrodes of said array of electrodes for electrical stimulation of the endometrium and/or endometrial cavity.

14. The system of claim 1, wherein said flexible structure comprises one or more components configured to release a substance upon electrical activation applied by one or more of said electrodes.

15. The system of claim 1, wherein said flexible structure lacks sufficient rigidity for insertion to said endometrial cavity without a delivery structure.

16. The system of claim 10, wherein, when a tip of said second end portion is positioned in proximity to a fundus of said endometrial cavity, said different regions include different regions with respect to a longitudinal dimension of said endometrial cavity;
   wherein said data acquisition and signal processing hardware is configured to determine said directionality of the uterine contractility with respect to said longitudinal dimension of said endometrial cavity using said plurality of measurements and relative positioning of said array of electrodes.

17. The system of claim 10, wherein said data acquisition and signal processing hardware is configured to characterize, using intensities of said plurality of electrical measurements of said electrical activity, whether said contractility is directed in a cephalad direction or a caudal direction.

18. The system of claim 1, wherein said flexible structure is ribbon shaped having a depth less than said width.

19. The system of claim 17 wherein, when a tip of said second end portion is positioned in proximity to a fundus of said endometrial cavity, said different regions include different regions with respect to a longitudinal dimension of said endometrial cavity;

wherein said data acquisition and signal processing hardware is configured to determine said directionality of the uterine contractility with respect to said longitudinal dimension of said endometrial cavity using said plurality of measurements and relative positioning of said array of electrodes.

* * * * *